United States Patent [19]

Nelson et al.

[11] 4,446,106
[45] May 1, 1984

[54] ANALYSIS SYSTEM

[75] Inventors: Larry A. Nelson; Leon W. Schmidt, both of Spokane, Wash.

[73] Assignee: Instrumentation Laboratory Inc., Lexington, Mass.

[21] Appl. No.: 339,331

[22] Filed: Jan. 15, 1982

[51] Int. Cl.³ .................. G01N 9/30; G01N 35/00
[52] U.S. Cl. .................. 422/72; 250/214 R; 356/427; 422/67; 436/45; 436/50
[58] Field of Search .................. 422/64, 67, 72, 73; 356/427; 364/499; 250/214

[56] References Cited

U.S. PATENT DOCUMENTS

| | | | |
|---|---|---|---|
| 3,470,367 | 9/1969 | Frisby | 235/183 |
| 3,555,284 | 1/1971 | Anderson | 356/427 |
| 3,576,441 | 4/1971 | Adams | 422/72 |
| 3,615,140 | 10/1971 | Doornekamp et al. | 356/427 |
| 3,748,044 | 7/1973 | Liston | 356/180 |
| 3,798,459 | 3/1974 | Anderson | 250/218 |
| 3,920,969 | 11/1975 | Berglas | 436/95 |
| 4,031,506 | 6/1977 | Siems | 340/15.5 |
| 4,043,756 | 8/1977 | Sommervold | 23/230 R |
| 4,052,161 | 10/1977 | Atwood | 23/230 R |
| 4,143,365 | 3/1979 | Cayzac | 340/347 |
| 4,226,537 | 10/1980 | Colley | 422/72 |
| 4,236,894 | 12/1980 | Sommervold | 23/230 R |
| 4,260,580 | 4/1981 | Sindo | 422/64 |

FOREIGN PATENT DOCUMENTS

2347464  4/1974  Fed. Rep. of Germany ...... 356/427

Primary Examiner—Michael S. Marcus

[57] ABSTRACT

A chemical analysis system for analyzing a plurality of independent specimens that have time varying characteristics includes a circumferential array of analysis regions that hold the specimens. The analytical regions are sequentially and repetitively sensed and resulting analysis signals corresponding to monitored specimen characteristics are stored in corresponding memory locations. A signal transmission channel connected between the sensor and the memory includes a signal storage capacitor and variable slew rate circuitry. The stored data signal value from the location in memory corresponding to the next analysis region to be sensed is applied to the signal transmission channel while the slew rate circuitry is set in a fast slew rate condition to preset the storage capacitor, and then the data signal generated by said sensor is applied to the signal transmission channel while the slew rate circuitry is set in a slow slew rate condition to adjust the data signal value in the storage capacitor to the current analysis signal value provided by the sensor.

9 Claims, 3 Drawing Figures

ANALYSIS SYSTEM

This invention relates to analytical systems and more particularly to analytical methods and apparatus for concurrently performing analyses on different specimens.

An accurate measurement of one or more constituents of a small volume of a biological fluid such as blood is frequently desired. For example, values of particular constituents of a blood sample may be useful in providing diagnostic information. Concurrent analysis of different specimens is often desirable. An example of such concurrent analyzer system is the centrifugal analyzer which is useful inter alia in performing kinetic and end point analyses. Such analyzers utilize a multicuvette rotor assembly which has an array of radially disposed cuvettes with an annular series of analysis regions at the outer ends of the cuvettes. The rotor is usually driven at a preliminary fast speed in the vicinity of 3000–5000 rpm for transfer and mixing of specimens and reagents in each cuvette, and then at a speed of approximately 1000 rpm for measurement of the chemical reactions in the several analysis regions. During such measurement, the analytical regions are sensed repetitively in rapid sequence. For example, in a twenty cuvette rotor that is driven at 1000 rpm during a measurement sequence, the successive cuvette analysis regions are sampled at three millisecond intervals and each cuvette analysis region is sensed several hundred times in a measurement sequence of less than thirty seconds duration. A common use of such analyzers is in the determination of biological fluid components, and the chemistry procedures that are performed include, but are not limited to, analyses for glucose, cholesterol, creatanine, total protein, calcium, phosphorous, and enzymes.

During a measurement sequence in such an analyzer, the sensor output signal rapidly alternates between low amplitude outputs (e.g., in intervals between analysis regions) and higher amplitude outputs (e.g., when radiation from an analysis region is being sensed). For these reasons, fast response (wide bandwidth) circuitry that adeqately follows the rapidly changing output signal from the sensor has been employed.

In accordance with an aspect of the invention, there is provided an analytical system for concurrently performing a plurality of analyses which includes a sensor arrangement for rapidly and repeatedly scanning a series of analytical regions. A main memory stores data output signals of values sensed from the analytical regions in corresponding memory locations. Between the sensor arrangement and the main memory is a signal transmission channel which includes signal storage means and variable slew rate circuitry. During each interval between sensing of analyses regions the variable slew rate circuitry is placed in its high slew (fast response) mode and an analog signal corresponding to a stored data signal is applied to the signal transmission channel to preset the signal storage to the signal level corresponding to the last stored signal for the analysis region next to be sensed. During each sensing interval, the variable slew rate circuitry is placed in a lower slew rate mode and the sensor signal is applied to the storage circuit to update the stored (preset) value. At the end of the sensing interval, the stored updated signal is transferred to the main memory for storage in a location corresponding to the sensed analytical region. Advantages of the invention include improved accuracy, improved noise immunity, and greater system dynamic range. With improved dynamic range, system power can be decreased with resulting cost reduction and increased reliability.

In a particular embodiment, the analytical regions are arranged in a circumferential array, and the scanning means includes means for spinning the array so that the analysis regions sequentially and repetitively pass the sensor. The sensor is a photomultiplier tube adapted to sense radiation from the analysis regions which represents time varying characteristics of the specimens. An amplifier, connected in circuit between the photomultiplier tube and the signal transmission channel, is arranged so that its gain may be adjusted to facilitate operation of the photomultiplier tube at an optimum signal level. The signal transmission channel is a unity gain circuit of the sample-and-hold type and includes a transconductance amplifier, and a temporary signal storage capacitor. The transconductance amplifier includes a variable bias input which enables its slew rate to be varied. While it will be apparent that other types of filter circuits may be used, this transconductance amplifier circuit provides economically effective results. A loop circuit for storing and feeding back data signals includes an analog to digital convertor connected in circuit between the output of the signal transmission channel and a random access memory and a digital to analog convertor connected in circuit between the memory and the input of the signal transmission channel.

Other features and advantages of the invention will be seen as the following description of a particular embodiment progresses, in conjunction with the drawings, in which.

DESCRIPTION OF PARTICULAR EMBODIMENT

Figure 1:
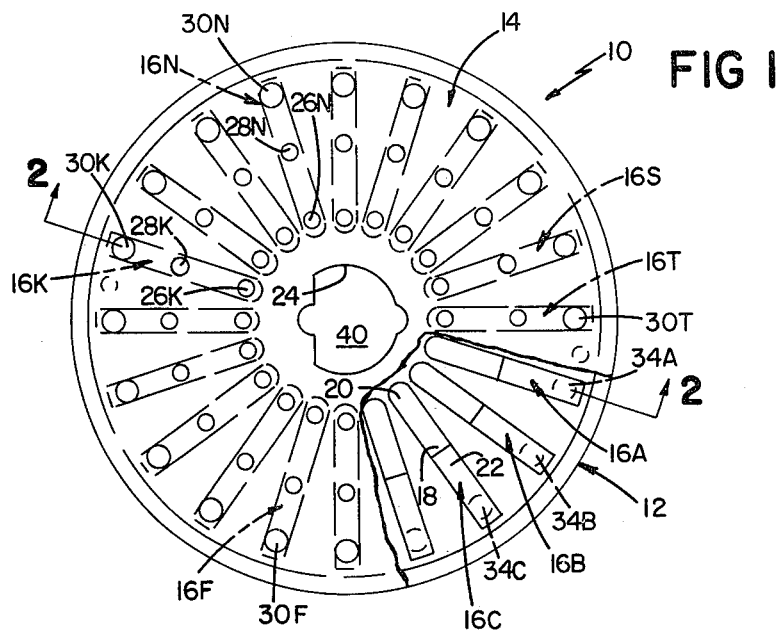
FIG. 1 is a top plan view of a rotor assembly for use in an analytical system in accordance with the invention.
Figure 2:
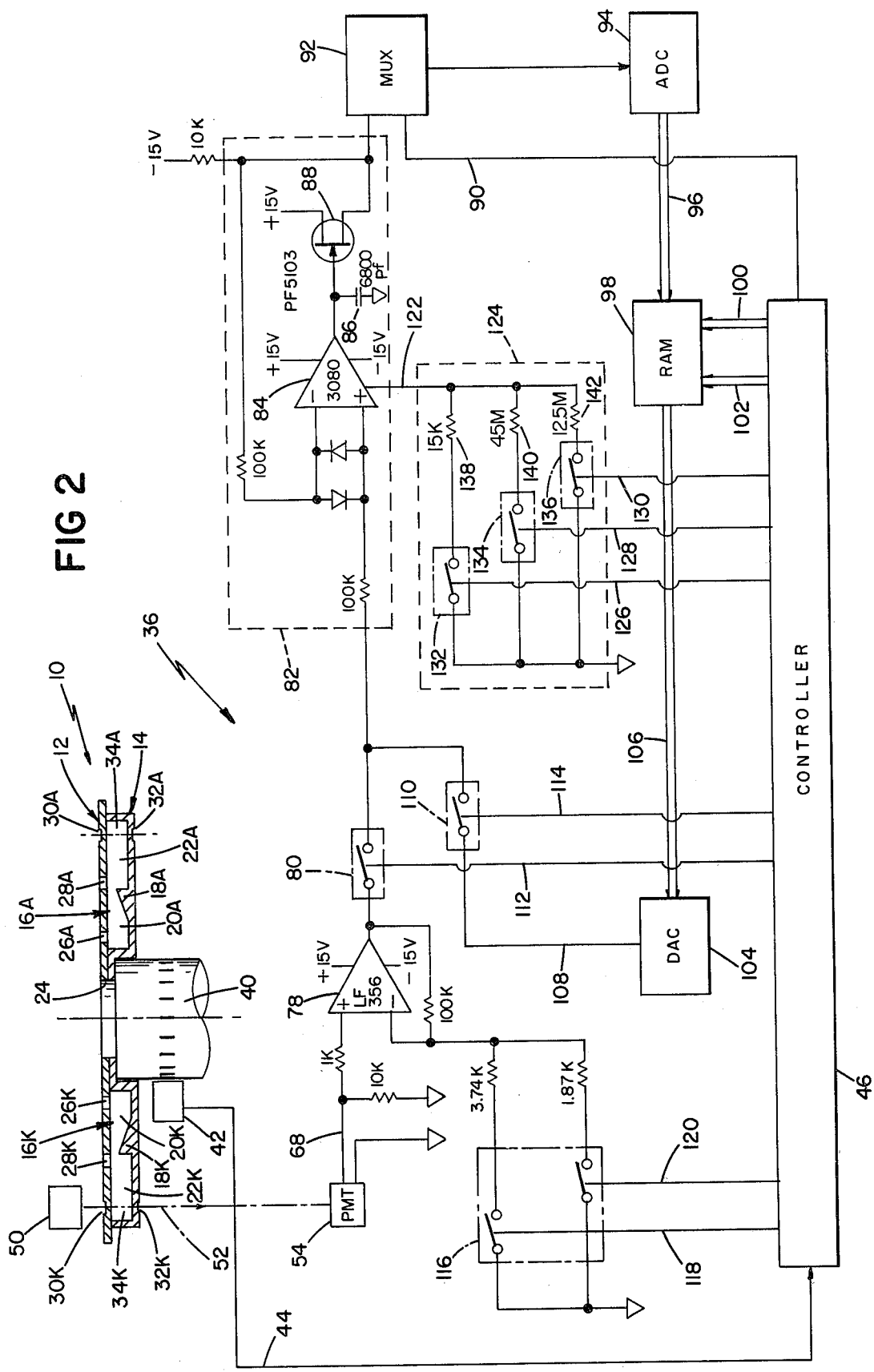
FIG. 2 is a diagrammatic view showing a cross-section of the rotor assembly of FIG. 1, together with signal processing components of the analytical system.

The multicuvette rotor assembly 10 shown in FIGS. 1 and 2 is of the type shown in U.S. Pat. No. 4,226,531 (incorporated herein by reference) and has a diameter of about ten centimeters and an overall height of about ¾ centimeter, and is formed of an injection molded acrylic body member 12 and an injection molded cover member 14, the body and cover members having the desired transparency, chemical resistance, and optical characteristics for photometric and fluorescence analyses.

Body member 12 defines a circumferential array of twenty individual cuvettes 16A–16T, each of which has a length of about four centimeters and a width of about ½ centimeter. Barrier structure 18 in each cuvette separates an inner chamber 20 from an outer chamber 22, each outer chamber 22 having a static capacity of about 250 microliters. Cover member 14 is a flat circular disc that has a substantially D-shaped central opening 24 which is aligned with a corresponding opening in body 12, circumferential array of inner loading ports 26 which communicate with corresponding inner chambers 20, a circumferential array of outer loading ports 28 which communicate with outer chambers 22, and a circumferential array of recessed optical windows 30 which are aligned with corresponding optical windows 32 in body member 12 such that an analysis region 34 is defined in each cuvette 16 (FIG. 2) that has an optical path length of ½ centimeter.

In this embodiment, a specimen to be analyzed of about 2-20 microliters volume is dispensed into chamber 20 and a reagent of about 150-200 microliters volume appropriate for the particular analysis is dispensed into chamber 22. After rotor 10 has been completely loaded, it is transferred to an analyzer unit 36 (FIG. 2) for incubation and analysis. In the analysis sequence, drive 40 brings rotor 10 up to a speed of 4000 rpm for about one second for transfer of sample (and reagent, if any) from chamber 20 to chamber 22 for mixing; then brakes rotor 10 to a full stop; and then drives the rotor at 1000 rpm for analysis. Analyzers of this type may utilize various photometric analyses, including, for example, absorbance, fluorescence, light scattering, and luminescence. Optical encoder 42 senses rotation of rotor module 10 and provides synchronizing signals over cable 44 to controller 46. Controller 46, which in a particular embodiment includes an Intel 8080 microprocessor, generates timing signals for control of the analytical sequence. It will be appreciated that various other types of controllers may be used in accordance with the invention.

The analysis system shown in FIG. 2 includes light source 50 and radiation from that source is directed along optical path 52 for passage through analysis regions 34 for sensing by photomultiplier 54. FIG. 3A of the timing diagram indicates the varying intensity of light beam 52 as rotor 10 is driven by drive unit 40. During the interval when the entire beam 52 is passing through an analysis region 34 (between optical windows 30 and 32), there is a flat interval or "window" 60. Partial blocking of the light beam 52 on either side of an analysis region 34 produces rising and falling transitions 62, 64. During intervals 66 between analysis regions 34, optical beam 52 is blocked. The relative shapes and dimensions of the transmitted radiation beam diagram of FIG. 3A are a function of factors such as the dimensions of analytical regions 34, the spacing between adjacent analytical regions, and the width of radiation beam 52, and it will be appreciated that such dimensional factors may vary widely without departing from the invention. The diagram of FIG. 3B illustrates corresponding outputs of photomultiplier tube 54 on line 68. The magnitude of these outputs alternates between data signal intervals 70 where the optical beam 52 is passing through an analysis region 34 and photomultiplier dark current intervals 72 where the optical beam 52 is not passing through an analysis region. The sensor output on line 68 varies in similar manner in other types of photometric analyses such as light scattering, luminescence, and fluorescence. As rotor 10 is spun by drive 40, analysis regions 34A-34T are sensed in sequence so that the series of spaced data signals 70 are repetitively produced. For example, when rotor 10 is spun at 1000 rpm, each cuvette analysis region 34 is sensed several hundred times in an analytical sequence of twenty-four seconds duration. The photomultiplier output signal on line 68 rapidly alternates between low amplitude output intervals 72 and higher amplitude output intervals 70. In the monitoring of a kinetic reaction, for example, the magnitude of the data signal output from a particular analytical cuvette changes between successive measurement intervals, the magnitude of that change being relatively small, as indicated diagrammatically in FIG. 3B, the signal level 74 representing the magnitude of the data signal output from that analysis region during the immediately preceding measurement interval. Typically, the difference in magnitude between successive readings from the same analysis region 34 (e.g., 70K and 74K) does not exceed 180 microvolts, while the difference between outputs from adjacent analytical regions (e.g., 70K and 70L) may be as great as ten volts.

With reference again to FIG. 2, the data signal output from photomultiplier 54 on line 68 is applied through amplifier 78 and switch 80 to a unity gain circuit 82 that includes variable slew rate amplifier 84 (RCA Type CA 3080), signal storage capacitor 86 and field effect transistor 88. In response to a signal from controller 46 over line 90, the stored signal is read through multiplex circuit 92 to analog to digital convertor 94 for application as a twelve bit binary value over line 96 to random access memory 98. Under the control of memory address signals on cable 100 and memory control signals (e.g., read, write) on cable 102 from controller 46, that binary data word is stored at an address in memory 98 allocated to data from the corresponding analysis region 34.

The system also includes a digital to analog convertor 104 to which a digital signal from memory 98 is applied over cable 106. The analog output signal from convertor 104 is applied over line 108 through switch 110 to the unity gain circuit 82. Switches 80 and 110 are alternately closed in response to signals on lines 112 and 114, respectively from controller 46 to alternately apply to the unity gain circuit 82 an analog signal from memory 98 via switch 110 and an amplified data signal from an analysis region 34 via switch 80.

The gain of amplifier 78 is adjusted by controller 46 via binary switch unit 116 (Type DG 201) in response to signals on line 118 and 120 to select an amplification factor correlated with the type of analysis being performed—enabling operation of photomultiplier tube 54 close to its optimal signal-to-noise operating point. Controller 46 also adjusts the slew rate of amplifier 84 via bias input 122 and a similar binary switch unit 124 which responds to controller signals on lines 126, 128, and 130 for closing switches 132, 134, and 136 respectively. When switched 132 is closed, resistor 138 is connected to bias input 122, placing transconductance amplifier circuit 84 in a high slew rate mode (about 150 millivolts per microsecond); when switch 134 is closed, amplifier circuit 84 is placed in a slow slew rate mode (about 55 microvolts per microsecond); and when switch 136 is closed, amplifier 84 is placed in an intermediate slew rate mode (about 180 microvolts per microsecond). It will be apparent that additional slew rate modes may be similarly provided, correlated, for example, with the reaction rate of the chemical reaction in a corresponding particular analysis region 34 of rotor 10.

Figure 3:
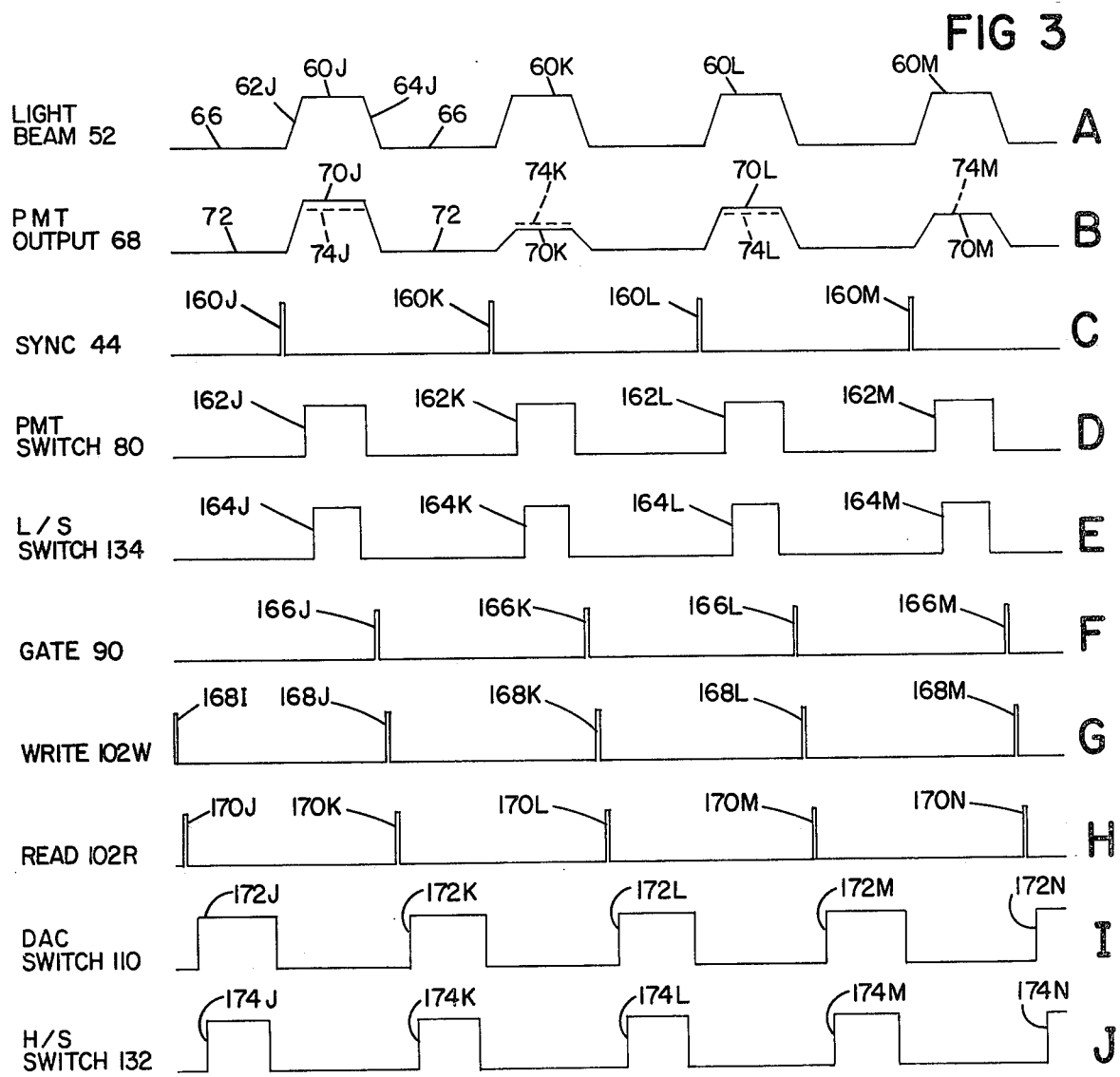
FIG. 3 is a timing diagram illustrating an operational sequence of the analytical system shown in FIG. 2.

Further understanding of the system may be had with reference again to the timing diagram of FIG. 3. That diagram indicates general and illustrative timing relationships and it will be apparent that those relationships may advantageously be adjusted for particular applications. A synchronizing pulse 160 from optical encoder 42 is transmitted over line 44 at the beginning of each analysis region sensing interval; and controller 46, in response to that synchronizing pulse, generates a sequence of signals—signal 162 on line 112 to close switch 80, signal 164 on line 128 to close switch 134, gating signal 166 on line 90, memory write signal 168 on cable 102, memory read signal 170 on cable 102, signal 172 on line 114 to close switch 110, and signal 174 on line 126 to close switch 132.

In each sensing interval, during the data "window" 60, switch 80 is closed so that the analysis region signal produced by photomultiplier tube 54 is applied to circuit 82. Prior to that data "window", capacitor 86 has been preset to the data value last sensed from that cuvette region 34 with circuit 82 in a high slew rate mode. During each data "window", circuit 82 may be placed in a low slew mode (high noise immunity) to respond to the relatively small signal differential between the previous data value and the current signal value from that analysis region. At the end of each sensing interval, circuit 82 is placed in a "hold" condition by opening the switches to bias input 122, and then the stored signal value, in response to gating signal 166 from controller 46, is read through multiplexer 92 to analog to digital convertor 94 and transformed into a twelve bit binary value which is stored in memory 98 in response to a write signal 168 at the memory address corresponding to the sensed analysis region (as identified by address signals on cable 100).

Controller 46 next generates signals on address lines 100 to identify the memory address in which is stored the immediately preceding data signal 74 for the next analysis region 34; and that data word is read from memory 98 in response to a read command 170 supplied over cable 102 and transferred over lines 106 to DAC 104. The resulting analog signal from DAC 104 is then applied to the input of circuit 82 when controller 46 closes switch 110 (signal 172). Signal 174 on line 126 closes switch 132 to connect resistor 138 to amplifier bias input 120, thus placing circuit 82 in a high slew rate condition. During this high slew rate interval capacitor 86 is preset to the data value provided by DAC 104 over line 108. Circuit 82 is then shifted to a low slew rate mode and the signal 70 indicative of the current value of the reaction from the analysis region 34, aligned with photomultiplier tube 54 is applied through switch 80 to adjust that preset value to the current data value. As this data value adjustment is performed in the low slew rate mode, this adjustment has high immunity to transients and other spurious signals, so that the signal stored on capacitor 86 is an accurate representation of the current status of the chemical reaction and is obtained during a relatively short sampling interval. In system use, it is frequently desirable to initially operate the system solely in high slew mode to store initial data values of the several different chemical reactions in analysis regions 34 in assigned corresponding locations in memory 98; and then to shift to the alternate high slew—low slew mode of operation described above.

With specific reference to FIG. 3, in response to read signal 170J, the data from the memory location corresponding to cuvette J is read out to DAC 104 and, when switch 110 is closed, the resulting analog signal value is applied to the input of circuit 82. Signal 174J closes switch 132 and places the circuit in its high slew rate mode to allow rapid shifting of the voltage from the previous voltage level to the voltage level provided by the analog signal applied to the input as indicated at 74J at FIG. 3B. At the beginning of the rising signal transition 62J, in preparation for reading a data value from analysis region 34J, switch 110 is opened and switch 80 is closed. Switch 134 is also closed, placing circuit 82 in a slow slew rate mode via its bias input 122. The data signal 70J is applied during the "window" interval 60J where there are no optical distortions due, for example, to partial blocking of optical beam 52, and circuit 82 in its low slew rate mode has enhanced immunity to transients and other spurious signals so that the current data signal 70J adjusts the preset value 74J stored on capacitor 86 to provide an accurate indication of that current data value. Prior to the end of "window" interval 60J, switch 130 is opened to place circuit 82 in a "hold" condition. Gating pulse 166J then transfers the stored data signal value to analog to digital convertor 94; and then controller 46 selects the memory address for analysis region 34J and generates write signal 168J to store the digital data value presented on lines 96 in that selected memory address.

The system thus records accurate reaction data from successive analysis regions in an arrangement which accommodates large variations in signal values and reaction rates between the several analytical regions while providing excellent noise immunity during measurement intervals. With the resulting improved noise immunity, system performance parameters such as high voltage power supply ripple for the photomultiplier tube and the light source can be relaxed and system dynamic range can be increased.

While a particular embodiment of the invention has been shown and described, various modifications of the invention will be apparent to those skilled in the art, and therefore it is not intended that the invention be limited to the disclosed embodiment or to details thereof and departures may be made therefrom within the spirit and scope of the invention.

What is claimed is:

1. A chemical analysis system for analyzing a plurality of independent specimens that have time varying characteristics comprising:
    a plurality of analysis regions, each said analysis region adapted to hold a corresponding specimen,
    scanning means including a sensor for producing an analysis signal having a value proportional to a characteristic of the specimen in an analysis region, and means for causing sequential and repetitive sensing of said analysis regions by said sensor to produce analysis signals having values corresponding to the monitored specimen characteristics in the several analysis regions,
    memory means for storing data values in locations corresponding to the analysis regions from which these data values were provided,
    a signal transmission channel for applying data value signals to said memory means, said signal transmission channel including temporary signal storage means and variable response circuitry having a fast response mode and a slower response mode, and
    control means connected to said variable response circuitry and operative during a first portion of an analysis region sensing interval for concurrently placing said variable response circuitry in said fast response mode and connecting said memory means to the imput of said signal transmission channel to preset said temporary signal storage means to a data signal value from that analysis region that has been previously stored in said memory means,
    and operative during a second portion of said analysis region sensing interval for concurrently placing said variable response circuitry in said slower response mode and connecting said sensor to said signal transmission channel to adjust the data signal value in said temporary signal storage means to the current analysis signal value provided by said sensor, and means for transferring said adjusted data signal value from said temporary signal storage means to a location in said memory means corresponding to that analysis region.

2. The system of claim 1 wherein said analytical regions are arranged in a circumferential array, and said scanning means includes means for spinning said array so that said analysis regions sequentially and repetitively pass said sensor.

3. The system of claim 1 wherein said sensor is a radiation sensor adapted to sense radiation from said analysis regions representative of said time varying characteristics, and further including an amplifier connected in circuit between said radiation sensor and said signal transmission channel, and means for varying the gain of said amplifier to operate said sensor at an optimum signal level.

4. The system of claim 3 wherein said radiation sensor is a photomultiplier tube.

5. The system of claim 1 wherein said signal transmission channel is a unity gain circuit.

6. The system of claim 1 and further including an analog to digital convertor connected in circuit between the output of said signal transmission channel and said memory means and a digital to analog convertor connected in circuit between said memory means and the input of the signal transmission channel.

7. The system of any one of claims 1-6 wherein said signal transmission channel includes a transconductance amplifier, said temporary signal storage is a capacitor and said variable response circuitry includes a variable bias input to said transconductance amplifier.

8. The system of claim 3 wherein said analysis regions are in the rotor of a centrifugal analyzer, said signal transmission channel includes a transconductance amplifier, said temporary signal storage is a capacitor and said variable response circuitry includes a variable bias input to said transconductance amplifier, and further including an analog to digital convertor connected in circuit between the output of said signal transmission channel and said memory means and a digital to analog convertor connected in circuit between said memory means and the input of said signal transmission channel, and wherein said control means includes a microprocessor for controlling the gain of said amplifier, said variable response circuitry, and said memory means.

9. The system of claim 1 wherein said variable response circuitry includes means to vary the slew rate of said signal transmission channel.

* * * * *